United States Patent [19]

Ayglon et al.

[11] Patent Number: 4,475,941
[45] Date of Patent: Oct. 9, 1984

[54] BIOCIDE COMPOSITION COMPRISING SULFONIUM COMPOUNDS AND ORGANIC TIN COMPOUNDS

[75] Inventors: Daniel Ayglon, Jurancon; Marie C. Hardy, Ortez, both of France

[73] Assignee: Societe Nationale Elf Aquitaine, France

[21] Appl. No.: 370,968

[22] Filed: Apr. 22, 1982

[30] Foreign Application Priority Data

Apr. 27, 1981 [FR] France ............................. 81 08350

[51] Int. Cl.$^3$ ............................................. A01N 55/04
[52] U.S. Cl. ........................................ 71/67; 424/288
[58] Field of Search ............................. 424/288; 71/67

[56] References Cited

U.S. PATENT DOCUMENTS

| | | | |
|---|---|---|---|
| 2,957,785 | 10/1960 | Leatherland | 117/138.5 |
| 3,082,230 | 3/1963 | Dorfelt et al. | 260/429.7 |
| 3,097,999 | 7/1963 | Koopmans | 424/288 |
| 3,311,649 | 5/1967 | Molt et al. | 424/288 |

FOREIGN PATENT DOCUMENTS

| | | | |
|---|---|---|---|
| 708847 | 6/1941 | Fed. Rep. of Germany . | |
| 1109444 | 6/1961 | Fed. Rep. of Germany | 424/288 |
| 2045337 | 4/1971 | Fed. Rep. of Germany | 424/288 |
| 810437 | 3/1937 | France . | |
| 1386350 | 12/1964 | France | 424/288 |
| 39-3045 | 3/1964 | Japan | 424/288 |
| 46-29747 | 8/1971 | Japan | 424/288 |
| 301027 | 9/1965 | Netherlands | 424/288 |
| 885848 | 12/1961 | United Kingdom | 424/288 |
| 946770 | 1/1964 | United Kingdom . | |
| 1023527 | 3/1966 | United Kingdom | 424/288 |

*Primary Examiner*—Allen J. Robinson
*Attorney, Agent, or Firm*—Ostrolenk, Faber, Gerb & Soffen

[57] ABSTRACT

Process for the destruction or/and inhibition of the growth of microorganisms by means of organic derivatives of tin to which is added a sulfonium function bearing compound, with or without a solvent, to obtain a synergistic effect. Application of the process for the treatment of an aqueous medium, natural or industrial, refrigeration circuit, underground water reinjection circuit, especially for assisted recovery in the petroleum industry.

16 Claims, No Drawings

BIOCIDE COMPOSITION COMPRISING SULFONIUM COMPOUNDS AND ORGANIC TIN COMPOUNDS

The invention concerns a process for the destruction or/and inhibition of the growth of microorganisms; it comprises compositions containing sulfonium compounds associated with organic derivates of tin. More especially, the invention concerns proportions of sulfonium and stannic derivates producing a synergistic effect in the destruction of microorganisms or/and the inhibition of their growth. Among its most important applications, this invention concerns biocide action on the microorganisms with which water and especially waste waters are infested.

At the present time, a large number of biocides are known which are applicable in different fields. In the special case of water disinfection, the importance of which is great for industry as well as for everyday uses, chlorine, ozone, organochlorinated compounds, organometallic derivatives, phénolic substances, sulfur or nitrogen compounds are widely used. All these agents, that are widely used, present advantages and drawbacks associated with their chemical and physico-chemical characteristics and their specificity of action. Consequently, there is still a need for biocides which can be used in as small quantities as possible and having a larger range of action.

One type of most useful biocides, which render notable service in different fields, including that of water, comprises organo-stannic compounds. Numerous publications have described such compounds; this is the case, for example, of German Pat. Nos. 1 084 722, 1 109 444 or U.S. Pat. No. 2 957 785. However, these substances are relatively expensive; furthermore, the accumulation of metallic derivatives is not generally desirable. Attempts have been made to use smaller quantities of tin compounds in association with quaternary ammonium salts, but the results have been somewhat disappointing: the duration of inactivity by such mixtures, for numerous microorganisms, is much shorter than with stannic derivatives and hardly any synergistic effect is observed. It does not appear, therefore, that improvement is possible through the association of organostannic compounds with tensio-active agents.

The present invention results from the unexpected observation that, despite hardly encouraging results mentioned above, it is possible to obtain a synergistic effect of an organo-stannic biocide with another biocide, provided this latter contains a sulfonium function. Remarkable results have been obtained in this manner, which lead to a sharp increase of the biocide power with a very appreciable saving of tin.

The new process, according to the invention, involves treating the medium, infested or infestable by harmful microorganisms, jointly with one or several organic derivatives of tin and at least one sulfonium compound.

According to the case and the circumstances, the tin derivative and that of sulfonium are simultaneously or separately added to the medium to be treated. Thus, may be introduced, in a certain aqueous medium, one or two synergising compounds, tin or sulfonium derivatives, allowing them to react during a certain time and, thereafter, the second of the compounds is introduced.

For simultaneous applications, according to the invention, of the two types of components, organic derivatives of tin can be mixed with the sulfonium compounds, in solution or suspension. The new synergistic composition, according to the invention, can thus be constituted by a pasty mixture or further by a solution in an appropriate solvent, a dispersion or aqueous emulsion or other. The emulsions are particularly advantageous, when aqueous solutions have to be sterilized.

The compositions according to the invention have very wide applications and a notable use is that of inhibiting the growth of microorganisms in water, possibly salt water and hard water. It is known, indeed, that deposits of biological origin act on different aqueous systems, especially lakes, ponds, rivers, bogs, swimming pools, etc. The same is true of industrial systems such as refrigeration circuits, industrial paper-mills, underground water reinjection, assisted recovery and the petroleum industry. The accumulation of germs in calm waters of such surfaces or circuits leads to the progressive deterioration by attack and corrosion of materials present; thus are corroded wood, metals, cements, etc.; furthermore, choking is produced of the pipes and organs such as pumps, thermal exchangers, valves and others, which renders exploitation difficult and increases maintenance costs. Thus, the process according to the invention is highly suitable to overcome these various drawbacks; in its preferred form, the appropriate quantity of a mixture according to the invention is introduced into the aqueous medium to be sterilized, as a solution or dispersion, the proportion of active constituents being preferably equal to or near those which provoke the maximum of synergistic action.

The organic compounds of tin, useful for the realisation of the invention, can be selected from among the stannous or stannic organic derivatives possessing biocide properties. More especially are suitable stannic compounds in which 1 to 3 hydrocarbon groups are linked to the tin atom, whereas the remaining valences of the tin atom are saturated by a metalloid, most often oxygen, sulfur or halogen, or indeed by a hydrocarbon radical. These compounds can be represented by the formula:

$$R_n SnZ_{(4-n)}$$

in which:
R is a preferably $C_1$ to $C_{12}$ alkyl, alkenyl, cyclo-alkyl, cyclo-alkenyl, aryl or alkyl-aryl radical ;
n is an integer equal to 1, 2 or 3;
Z represents a metalloid, principally S, O, Cl, Br, I or F.

Particularly useful are oxides, sulfides and halides of trialkyl- or triaryl tin. These are especially compounds such as $(R_3Sn)_2O$, $(R_3Sn)_2S$, $R_3SnX$ wherein X is a halogen. Preferred R alkyls are $C_1$ to $C_{12}$ alkyls; but they can be replaced by a phenyl. Z can also be a linear or branched alkyl, alkenyl, cyclo-alkyl, cyclo-alkenyl, aryl, alkyl-aryl radical, or an organic acid rest bearing a linear or branched, cyclo-alkyl, cyclo-alkenyl, aryl or alkyl-aryl; particularly efficient are the acetate, propionate, or benzoate of tributyl-tin, this last being $BU_3SnOCOC_6H_5$ called TBTB.

The sulfonium compounds used can be those which, according to the prior art, especially German Pat. No. 708 847 and French Pat. No. 810 437, are described as bactericides or fungicides. They are compounds of the type:

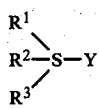

in which $R^1$, $R^2$ and $R^3$ are similar or different hydrocarbon groups and Y is an anion, especially a halogen or alkyl sulfate. Although groups $R^1$ to $R^3$ can have different constitutions, they are preferably $C_8$ to $C_{22}$ alkyls. Remarkable results are obtained when at least 1 of the 3 alkyls, similar or different, has 12 to 18 carbon atoms; maximum efficiency is obtained when $R^2$ is a tetradecyl, $R^1$ and $R^3$ being lower alkyls. The anion which is above all most suitable for use in the present invention is methosulfate.

Although the useful effects for synergy, between the tin containing biocides and those bearing a sulfonium function, appear for all substantial proportions of the compounds involved, there exists a certain optimum proportion that is worthwhile taking into account. Generally, the best results are obtained by using about 1 to 3 molecules of sulfonium for 1 atom of Sn; the best results are obtained when this ratio is close to 2, i.e. when there are 1.5 to 2.5, or better still 1.8 to 2.2 sulfonium functions per Sn atom. In the particular case of methosulfate of tetra-decyl-methyl sulfonium (SUL) associated with tributyl-tin oxide (TBTO), these preferential proportions are expressed by weight limits of 65 to 75 parts sulfonium for respectively 35 to 25 parts Sn compounds.

Of course, besides these two types of compounds defined by the present invention, i.e. sulfonium and organotin, other biologically active or non-active compounds can be used in the new compositions according to the invention. Thus, it can be advantageous to add to the composition one or more ionic or non-ionic tensioactive agents. Among these latter agents, quaternary ammonium salts are highly recommendable, since they allow at the same time to widen the range of biocide action of the mixture.

Quaternary ammonium compounds to be used are, for example, lauryl dimethyl benzyl ammonium chloride, octyl dimethyl benzyl ammonium chloride; decyl dimethyl benzyl ammonium bromide, stearyl dimethyl benzyl ammonium bromide, stearyl dimethyl ethyl ammonium bromide, lauryl dimethyl benzyl ammonium saccharinate or linoleyl diethyl hexyl ammonium, saccharinate, etc.

Other additives, of various natures, especially fungicides, can be associated with the compositions of the invention. These are, for example, derivatives of quinoline such as orthoxy-quinoline sulfate, guanidine salts, especially guanidine dodecyl acetate, methyl-oxo-dithiooloquinoxaline, pyrimidines, thiadiazines, as for example, thiazolyl-benzimideazole or dimethyl-tetrahydro thiadiazine thione, or other known biocides.

In order to illustrate the invention, some examples of applications of the new biocide synergistic compositions are non-limitatively described, in the particular cases in which the sulfonium is tetra-decyl dimethyl-sulfonium methosulfate

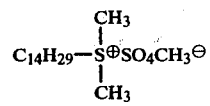

designated by the letters SUL, whereas the organo-stannic derivative is tributyl-tin oxide

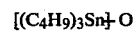

known as TBTO.

Tests were carried out on water of the French river called "Gave de Pau" which contains numerous microorganisms and which is widely used in industry to feed refrigeration circuits. It is through this water that are inseminated the classic nutrient mediums in the tubes used in these tests.

The total number of germs found in "Gave de Pau" water, is comprised between $10^5$ and $10^7$ per ml. The following microorganisms have been identified in this water, Bacteria: Enterobacteriaceae, Pseudomonaceae, Bacteriaceae, Clostridiales, Bacillales, Sporovibrionales,
Algae: Diatomees, Cyanophycees, Chlorophycees,
Fungi: Aspergillus.

EXAMPLE 1

To the bacteria contained in a peptonic culture, are added increasing quantities of the biocide substance to be studied. A control tube contains no biocide. Every three minutes, the optical density of the contents of the tubes of culture is determined; this operation is carried out at 30° C., under constant stirring, the tubes being placed in a biophotometer. Thus, the growth of the germs is evaluated. Table I shows the durations of inactivity, by the compounds used, of the microorganisms in the tubes treated as indicated hereinabove. A biocide is more efficient when the latency time is long and the growth are low; it is generally admitted that after latency time of 48h, all the germs are killed.

Table I shows the SUL active compounds, i.e. sulfonium described herein-above, used in a aqueous solution and the stannic compound TBTO in a 10 g/l solution in dimethyl-formamide. By way of comparison, tests were also carried out with alkyl-benzyl-dimethylammonium chloride, designated by AMQ,

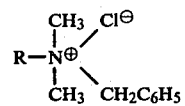

(product known in commerce under the name Benzalkonium). The two last lines of the table correspond to the mixtures of TBTO with AMQ and SUL+TBTO+AMQ used in a 10 g/l solution in dimethylformamide.

Dimethylformamide, used as solvent, in the above-mentioned tests, was found to be completely inactive. In order to achieve this it was established that dimethyl formamide, applied alone in the quantity corresponding to that which contains the 70 ppm TBTO solution, does not provoke any destruction of germs in the same conditions. It is thus possible to ignore its presence in the conclusions to be drawn from Table 1.

The above results show a remarkable activity of the 71.4 SUL+28.6 TBTO mixture which—as can be seen—for a quantity of 50 ppm, leads to a latency, i.e. inactivity, of the microorganisms during more than 48 h, which is not obtained in any other of the tests carried out. Indeed, for five other mixtures or active products, the latency of more than 48 h is obtained only with more than 60 ppm.

TABLE 1

| Active compounds | Duration of inactivity in hours Quantities ppm | | | | | | | |
|---|---|---|---|---|---|---|---|---|
| | 10 | 20 | 30 | 40 | 50 | 60 | 70 | 80 |
| SUL alone | | | | | 15 | 15 | 25 | 25 >48 |
| TBTO alone | | <5 | <5 | 5 | 5 | >48 | >48 | |
| AMQ alone | 5 | 5 | | 10 | | >48 | | |
| SUL 57% TBTO 43% | | | | 10 | 25 | >48 | >48 | |
| SUL 71.4% TBTO 28.6% | | | | 30 | >48 | >48 | >48 | |
| SUL 80% TBTO 20% | | | | 20 | 40 | >48 | >48 | |
| TBTO 28.6% AMQ 71.4% | | | | 0 | 0 | 0 | 15 | |
| SUL 35.7% TBTO 28.6% AMQ 35.7% | | | | 0 | 25 | >48 | >48 | |

It will be noted that this improved synergistic mixture comprises a quantity of only $(50 \times 28.6)/100 = 14.3$ ppm of TBTO stannic compound, which thus represents a very substantial tin saving and, furthermore, also of sulfonium; in fact, Table 1, shows that with TBTO alone, the same result would only be achieved with more than 60 ppm and, with SUL alone, above 80 ppm.

Another surprising result is that the AMQ quaternary ammonium compound alone must be used in a quantity of 60 ppm in order to produce an inactivity of more than 48 h, and that its mixture with TBTO gives rise to inactivity during only 15 h for 70 ppm.

It is thus seen that the three SUL+TBTO mixtures, and above all the second one, give rise to considerably improved results with respect to the other biocides tested.

EXAMPLE 2

The same active products as those of Example 1 are tested with a view to determining the effects of synergy after 24 h. Thus the doses necessary to produce inhibition of the flora studied in 24 h are determined. Table 2 summarizes the results of these tests and indicates the values of the synergistic actions S calculated according to the known synergy criterion method.

Criteria of Synergy

When two compounds 1 and 2, or three, 1, 2, 3 are mixed with a view to their joint use as a biocide, the synergistic action S of the mixture is expressed as:

$$\frac{Q_1'}{Q_1} + \frac{Q_2'}{Q_2} = S_{1-2} \text{ or } \frac{Q_1'}{Q_1} + \frac{Q_2'}{Q_2} + \frac{Q_3'}{Q_3} = S_{1-2-3}$$

in which the symbols Q designate the quantities necessary for the obtention of the desired result:
$Q_1$ when compound 1 is used alone,
$Q_1'$ when compound 1 is mixed with 2,
$Q_2$ when compound 2 is used alone,
$Q_2'$ when compound 2 is mixed with 1,
$Q_3$ when compound 3 is used alone,
$Q_3'$ when compound 3 is mixed with 1 and 2.

It is understood that the values of S lower than 1 signify that there is synergy between the compounds of the mixture: there is simple additivity of the actions when $S=1$; the values of S higher than 1 signify that there is an antagonism between the effects of the components of the mixture.

The last vertical column of Table 2 herein-under shows the three SUL+TBTO mixtures all produce marked effects of synergy and it is again the average mixture, i.e. SUL 71.4+TBTO 28.6 which is, from this point of view, the most efficient, since its synergy effect $S_{(1-2)}$ is equal to 0.55.

On the other hand, the penultimate horizontal line of the Table shows clearly that AMQ quaternary ammonium not only does not produce a synergistic effect with TBTO tin compound, but even produces an antagonistic effect with respect to the latter, since $S_{(2-3)}$ amount to 1.16; furthermore, it is seen that quantities above 70 ppm of this mixture are needed to reach inhibition after 24 h.

An interesting result appears from the last horizontal line of the Table 2, which shows that—despite the antagonism between TBTO and AMQ—a synergistic effect can however be obtained due to the addition of sulfonium. Although this effect $S_{(1-2-3)} = 0.76$ is lower than that of the first mixture SUL 57+TBTO 43, it is nevertheless interesting and underlines the unexpected character of the invention. Definitely, the ternary compositions of sulfonium and organic derivative of tin to which quaternary ammonium is added enter within the framework of the compositions according to the invention.

TABLE 2

| active compounds | dose ppm | Synergistic effects S for 24 h | | | |
|---|---|---|---|---|---|
| | | $\frac{Q_1'}{Q_1}$ | $\frac{Q_2'}{Q_2}$ | $\frac{Q_3'}{Q_3}$ | $S_{1-2}, S_{2-3}$ or $S_{1-2-3}$ |
| SUL alone | 80 = $Q_1$ | | | | |
| TBTO alone | 60 = $Q_2$ | | | | |
| AMQ alone | 60 = $Q_3$ | | | | |
| SUL 57% TBTO 43% | 28.6 = $Q_1'$ 21.4 = $Q_2'$ 50.0 | 0.36 | 0.36 | | 0.72 |
| SUL 71.4% TBTO 28.6% | 23.6 = $Q_1'$ 11.4 = $Q_2'$ 40.0 | 0.36 | 0.19 | | 0.55 |
| SUL 80% TBTO 20% | 40.0 = $Q_1'$ 10.0 = $Q_2'$ 50.0 | 0.50 | 0.17 | | 0.67 |
| TBTO 66.6% AMQ 33.3% | 20 = $Q_2'$ 50 = $Q_3'$ 70 | | >0.33 | >0.83 | >1.16 |
| SUL 35.7% TBTO 28.6% AMQ 35.7% | 17.9 = $Q_1'$ 14.2 = $Q_2'$ 17.9 = $Q_3'$ 50.0 | 0.22 | 0.30 | 0.24 | 0.76 |

EXAMPLE 3

Determinations analogical to those of Example 2 are carried out during 48 h. The results compiled in Table 3 confirm those of example 2: they show that after 48 h, the synergy effect is obtained with mixtures containing both sulfonium and tin compound. The maximum synergistic effect $S = 0.69$ is obtained with the mixture of 71.4% SUL and 28.6% TBTO. About 50 ppm of this optimal mixture is needed in order to stop the development of the germs during a time period of more than 48 h. The same effect can be produced by mixtures containing 57% and 80% SUL, provided they are used in quantities of 60 ppm. This latter quantity is also sufficient for the mixture of the ultimate line of the Table, which corresponds to a composition containing as much AMQ quaternary ammonium as sulfonium; however, in this last case, S reaches 0.92, which thus means that the synergy effect is rather weak.

With regard to the mixture without SUL, composed simply of TBTO and AMQ, more than 70 ppm is necessary and the activity of the biocide is reduced; there is no synergy since $S > 1.16$.

EXAMPLE 4

River water to which is added increasing quantities of biocide substances is passed through filters having a mesh of 0.2 microns. These filters which retain the bacteria are thereafter put to culture on standard gelo-sized mediums, for total germs, according to the Sartorius method.

The same SUL and TBTO compounds are used as in the preceding examples, TBTO being in solution in methanol. Furthermore the compounds are tested alone and as a mixture in water; in the last case, each of the constituents is introduced separately into the water to be studied.

TABLE 3

Synergistic effects during 48 h

| active compounds | Dose ppm | $\frac{Q_1'}{Q_1}$ | $\frac{Q_2'}{Q_2}$ | $\frac{Q_3'}{Q_3}$ | $S_{1-2}$, $S_{2-3}$ or $S_{1-2-3}$ | |
|---|---|---|---|---|---|---|
| SUL alone | 80 = $Q_1$ | | | | | |
| TBTO alone | 60 = $Q_2$ | | | | | |
| AMQ alone | 60 = $Q_3$ | | | | | |
| SUL 57% | 34.3 = $Q_1'$ | 0.43 | | | | |
| TBTO 43% | 25.7 = $Q_2'$ | | 0.43 | | 0.86 | |
| | 60.0 | | | | | |
| SUL 71.4% | 35.7 = $Q_1'$ | 0.45 | | | | |
| TBTO 28.6% | 14.3 = $Q_2'$ | | 0.24 | | 0.69 | |
| | 50.0 | | | | | |
| SUL 80% | 48.0 = $Q_1'$ | 0.60 | | | | |
| TBTO 20% | 12.0 = $Q_2'$ | | 0.20 | | 0.80 | |
| | 60.0 | | | | | |
| TBTO 28.6% | >20.0 = $Q_2'$ | | >0.33 | | | |
| AMQ 71.4% | >50.0 = $Q_3'$ | | | >0.83 | >1.16 | |
| | >70.0 | | | | | |
| SUL 35.7% | 21.4 = $Q_1'$ | 0.27 | | | | |
| TBTO 28.6% | 17.20 = $Q_2'$ | | 0.22 | | | |
| AMQ 35.7% | 21.4 = $Q_3'$ | | | 0.36 | 0.92 | |
| | 60.0 | | | | | |

The river water used contains $10^5$ germs per ml. After 48 h contact between the biocide and the water, and thereafter 48 h of culture, the following destruction percentages are found with different biocides tested:

| | |
|---|---|
| 30 ppm SUL | 99.99% |
| 20 ppm SUL | 99.90% |
| 100 ppm TBTO | 99% |
| 10 ppm mixture 71.4 SUL + 28.6 TBTO | 99.90% |

It was assured that methanol, at the quantity corresponding to that which contains the TBTO solution at 150 ppm, does not provoke any destruction of the germs.

It is also seen that the SUL-TBTO mixture has an efficiency notably higher than that of the agents taken separately, since it allows the practically complete destruction in water with only 10 ppm, whereas clearly higher doses are necessary of each of these constituents taken separately.

By comparing those results with those of Tables 2 and 3, it is possible to observe that TBTO is a contact biocide for the germs present in water, that it inhibits their growth, but does not necessarily produce their destruction. On the contrary, SUL has a more marked destructive effect, but necessitates larger quantities in order to inhibit the totality of the germs. The use of these two compounds jointly makes it possible to benefit from the addition of the two biocide effects.

Present Example 4 also shows that the synergistic action of the products used is not modified due to the separate introduction of SUL and TBTO: this confirms the efficiency of the variation of the process according to the invention, that consists in successively applying to the medium to be treated, the different constituents of the synergistic composition. Furthermore, it is observed that various solvents can be used in the realisation of the invention.

EXAMPLE 5

Application to the Water of a Petroleum Deposit

A mixture is prepared as follows:

| % | |
|---|---|
| 5.6 | TBTO |
| 14.0 | SUL |
| 5.6 | chloroform |
| 19.0 | non-ionic surfactant, namely ethoxylated alkylphenol |
| 55.8 | isopropanol |

This mixture has the property of being dilutable in any proportion with fresh water or salt water having various salinities, especially up to 50 g NaCl/l, as well as with hard waters between 0° and 40° TH.

The biocide action of this composition is determined by using the method described in Example 1, i.e. the control of bacteria development by biophotometry, river water being replaced herein by that of a contaminated petroleum deposit.

It is noted that the active substances of the above product hereinabove produce a biocide synergy effect.

The observation of the growth of the germs during 48 h shows that the SUL and TBTO products, applied separately, are not active up to large quantities, especially 400 ppm for TBTO. On the contrary, in the same conditions, the composition above described, which contains both active products, already act at a quantity of 50 ppm, i.e. 10 ppm of active products, of which 2.8 ppm TBTO and 7.2 SUL. The joint presence of these two compounds thus shows an extraordinarily improved result.

EXAMPLE 6

Since the sensivity to toxic elements of the different microorganisms can vary widely according to the species, it is interesting to determine the activity of the products according to the invention with respect to certain species taken individually.

Therefore, studies were made on the quantities necessary for the destruction, separately, of Gram+ and Gram− bacteria and fungi. The typical species subjected to the tests were:

Bacillus subtilis (G+) herein-after called SUBTILIS,
Pseudomona aeroginosa (G−) herein-after called PSEUDOMONAS,
Aspergillus niger (fungi)- herein-after called ASPERGILLUS.

In addition to the SUL and TBTB compounds of the previous examples, experiments were made on tin tributyl benzoate $(C_4H_9)_3SnOCOC_6H_5$, denoted by the initials TBTO in Table 4.

SUL - TBTO and SUL - TBTB mixtures are used as 20% solution in hexylene glycol.

Table 4 shows the results obtained from these tests.

This table makes apparent the synergistic/biocide effects of the mixtures according to the invention for all three of the species tested; indeed, coefficient S is always lower than or close to 1.

It is noted that for *Aspergillus niger* the biocide activity is complementary.

TABLE 4

| Active compounds | Necessary quantity in ppm | | | Coefficient of synergy S | | |
|---|---|---|---|---|---|---|
| | Subtilis | Pseudo-monas | Asper-gillus | Sub-tilis | Pseudo-monas | Asper-gillus |
| SUL alone | 1 | 63 | 6.25 | | | |
| TBTO alone | 0.08 | >500 | 0.05 | | | |
| TBTB alone | 0.31 | >500 | 0.05 | | | |
| SUL 75% TBTO 25% | 0.16 | 63 | 0.2 | 0.62 | <0.8 | ≅1 |
| SUL 75% TBTB 25% | 0.31 | 63 | 0.2 | 0.48 | <0.8 | ≅1 |

On the contrary, the synergy effect is particularly noticeable in the case of the PSEUDOMONAS that strongly resist the stannic compound alone, but are sensitive to the mixture according to the invention.

A result of the tests carried out is that the compositions according to the invention allow a considerable widening of the range of activity of the biocides; this confirms, furthermore, the results of the previous examples, carried out on mediums comprising a very complex flora.

EXAMPLE 7

A mixture constituted by 5% tin tributyl oxide (TBTO) and 15% tetradecyl dimethyl sulfonium metho-sulfate is placed in an oven at 50° C. during 4 days. Thin layer chromatographic method is applied for measuring the dibutyl tin that is produced by the decomposition of TBTO. The dibutyl tin content is lower than 1% which shows the stability of the mixture; this mixture thus presents a very special interest for its application in refrigeration circuits.

We claim:

1. A process of controlling the growth of the bacteria Enterobacteriaceae, Pseudomonaceae, Bacteriaceae, Clostridiales, Bacillales, or Sporovibrinoales, and the algae Diatomees, Cyanophycees or Chlorophycees, in aqueous medium which comprises introducing into the medium a biocidal effective amount of a synergistic mixture of 20 to 43 weight percent organic tin compound selected from the group consisting of tributyl tin oxide and tributyl tin benzoate and 80 to 57 percent by weight of tetradecyl dimethyl sulfonium methosulfate.

2. The process according to claim 1 wherein the organic tin compound is tributyl tin oxide.

3. The process of claim 2 in which said mixture contains 25-35% organic tin compound.

4. The process of claim 1 wherein the amount of said mixture introduced is 20 to 70 ppm.

5. The process according to claim 2 in which said mixture contains 20% of said organic tin compound.

6. The process of claim 5 wherein the amount of said mixture is 40-70 ppm.

7. The process according to claim 2 wherein said mixture contains 28.6% of organic tin compound.

8. The process according to claim 7 wherein the amount of said mixture is 40-70 ppm.

9. The process according to claim 2 in which said mixture contains 43% of said organic tin compound.

10. The method of claim 9 wherein the amount of said mixture is 40-70 ppm.

11. A biocidal composition comprising a synergistic mixture of 20 to 43 weight percent organic tin compound selected from the group consisting of tributyl tin oxide and tributyl tin benzoate and 80 to 57 percent by weight of tetradecyl dimethyl sulfonium methosulfate.

12. The composition according to claim 11 wherein the organic tin compound is tributyl tin oxide.

13. The composition of claim 12 in which said mixture contains 25-35% organic tin compound.

14. The composition according to claim 12 in which said mixture contains 20% of said organic tin compound.

15. The composition according to claim 12 wherein said mixture contains 28.6% of said organic tin compound.

16. The composition according to claim 12 wherein said mixture contains 43% of said organic tin compound.

* * * * *